United States Patent [19]

Thurow

[11] Patent Number: 4,783,441

[45] Date of Patent: Nov. 8, 1988

[54] AQUEOUS PROTEIN SOLUTIONS STABLE TO DENATURATION

[75] Inventor: Horst Thurow, Kelkheim, Fed. Rep. of Germany

[73] Assignee: Hoechst Aktiengesellschaft, Frankfurt am Main, Fed. Rep. of Germany

[21] Appl. No.: 564,346

[22] Filed: Dec. 21, 1983

Related U.S. Application Data

[63] Continuation of Ser. No. 263,720, Jun. 14, 1981, abandoned, which is a continuation-in-part of Ser. No. 144,040, Apr. 28, 1980, abandoned.

[30] Foreign Application Priority Data

Apr. 30, 1979 [DE] Fed. Rep. of Germany ....... 2917535
Dec. 22, 1979 [DE] Fed. Rep. of Germany ....... 2952119

[51] Int. Cl.$^4$ .................. A61K 37/00; A61K 37/26
[52] U.S. Cl. ........................................ 514/3; 514/2; 424/94.3
[58] Field of Search ........................................ 514/2, 3

[56] References Cited

U.S. PATENT DOCUMENTS

| | | | |
|---|---|---|---|
| 4,073,886 | 1/1973 | Kehm | 260/112 B |
| 4,129,560 | 12/1978 | Zoltobrocki | 260/112 R |
| 4,153,689 | 5/1979 | Hirai et al. | 424/178 |
| 4,179,337 | 12/1979 | Davis et al. | 424/178 |

FOREIGN PATENT DOCUMENTS

| | | |
|---|---|---|
| 205398 | 5/1956 | Australia . |
| 262351 | 7/1963 | Australia . |
| 39304 | 7/1965 | Australia . |
| 405608 | 1/1967 | Australia . |
| 410460 | 1/1969 | Australia . |
| 2212695 | 9/1973 | Fed. Rep. of Germany . |
| 1449333 | 9/1976 | United Kingdom . |
| 1554157 | 10/1979 | United Kingdom . |
| 1563311 | 3/1980 | United Kingdom . |

OTHER PUBLICATIONS

Chemical Abstracts 81 (26) 176134h & 176135j (1974).
Chemical Abstracts (80) (1974) 22796t.
Cecil et al., Biochem. J. (1970) 117, 147–156.
Schobert et al., Biochim. et Biophys. Acta (1978) 541, 270–277.
"Insulin, etc.", Proc. 2nd Intnl. Insulin Symposium, 9/4–7/79, de Gruyter, Berlin (1980) pp. 215–221.
The Merck Index, Merck & Co., Rahway, N.J. (1976) p. 1261.
Advances in Protein Chemistry, vol. 23, Academic Press, New York (1968) pp. 121–122, 211–217.
A Physico-Chemical Approach to the Denaturation of Proteins, Joly, Academic Press, New York (1965) pp. vii–ix, 30–36.

*Primary Examiner*—Frederick E. Waddell
*Attorney, Agent, or Firm*—Curtis, Morris & Safford

[57] ABSTRACT

What are disclosed are a method for preventing the denaturation of proteins such as insulin in aqueous solution at interfaces by the addition to the solution of a surface-active substance comprising a chain of alternating weakly hydrophobic and weakly hydropholic zones, protein solutions containing such a surface-active substance, methods of purifying proteins contained in such solutions, and methods of treating surfaces with such a surface-active material to prevent the denaturation of proteins thereon.

8 Claims, No Drawings

AQUEOUS PROTEIN SOLUTIONS STABLE TO DENATURATION

This is a continuation of application Ser. No. 263,720 filed May 14, 1981 and now abandoned, which is in turn a continuation-in-part of application Ser. No. 144,040 filed Apr. 28, 1980 and now abandoned.

This invention relates to an aqueous protein solution which is stable to denaturation of the proteins at interfaces and to processes for the manufacture of such a solution and for treating surfaces having a denaturing effect on protein solutions.

It is known that dissolved proteins are adsorbed at hydrophobic interfaces (including the interface aqueous solution/air) [cf. C. W. N. Cumper and A. E. Alexander, Trans. Faraday Soc. 46, page 235 (1950)]. Proteins are amphiphiles, that is to say they contain both hydrophilic and hydrophobic groups. The hydrophobic groups establish the contact to the hydrophobic interface.

Various secondary reactions are observed as a result of the adsorption of the proteins at interfaces, which reactions are generally embraced by the term "denaturation". A change in form of adsorbed protein molecules takes place (change of tertiary and/or secondary structure). In addition, adsorbed protein molecules may aggregate to soluble or insoluble polymeric forms. It is known that many proteins aggregate at surfaces, whereby the solutions become turbid or the proteins are biologically inactivated, which can be observed when stirring or shaking the aqueous solutions [cf. A. F. Henson, I. R. Mitchell, P. R. Musselwhite, J. Colloid Interface Sci. 32, page 162 (1970)]. This surface adsorption and aggregation is particularly disadvantageous in apparatus for the transport of protein solutions, for example automatic dosing devices for medicaments. In some cases even chemical reactions take place between the adsorbed proteins and dissolved substances [cf. F. MacRitchie, H. Macromol. Sci., Chem. 4, page 1169 (1970)].

This is especially the case with bovine, swine and human insulins or the De-B1-phenylalanine derivatives thereof. With a zinc content of up to 0.8%, based on the weight of insulin, they dissolve in aqueous media to give a clear solution at a pH below 4.3 and above 6.5. The said insulins form aggregates in aqueous solution so that the solution represents an equilibrium state of monomeric, dimeric, tetrameric, hexameric and oligomeric insulin molecules. It is known that insulin is adsorbed strongly at hydrophobic surfaces, which also include the solution/air interface [cf. Weisenfeld et al., Diabetes 17, page 766 (1968) and Browne et al., Eur. J. Biochem. 33, page 233 (1973)]. Experiments have shown that the adsorbed insulin can be denatured at the surface. This process is influenced by temperature and motion of the solution. The denatured product is desorbed again as a polymeric aggregate and, in a sufficiently high concentration in the solution, separates as a precipitate or forms a thixotropic gel. The denatured insulin is biologically inactive and may block feed tubes, for example in an insulin infusion pump which operates continuously or intermittently, as used, for example, in artificial beta cells.

In addition, the denatured insulin can give rise to immunological intolerances. Investigations have been published which make the physical form of insulin responsible for the formation of antibodies against insulin [cf. Kumar et al., Horm. Metab. Res. 6, page 175 (1974)]. Moreover, it is known that even human insulin, when administered to humans, may lead to immunological reactions [cf. A. Teuscher et al., Diabetologia 13, page 435 (1977)].

Aqueous insulin solutions for therapeutic purposes prepared according to the prior art can contain, in addition to the active substance, that is to say bovine insulin or swine insulin or a De-B1-phenylalanine derivative of these insulins, dissolved zinc in an amount of up to 0.8%, based on the weight of insulin, an agent for rendering these solutions isotonic, such as sodium chloride, glycerol or glucose, a preservative, such as phenol, cresol or methyl p-hydroxybenzoate, and a salt to buffer the pH value, such as sodium phosphate, acetate or citrate. Depot assistants, such as protamine or Surfen, can also be added in order to achieve a delayed insulin action, or these solutions are mixed withh crystalline or amorphous depot forms of the insulin. It has been found that dissolved insulin is denatured at interfaces in all of these preparations. Experiments have also shown that the rate of denaturation rises with a rising temperature, increased motion of the solution and a rise in the pH value of the solution. Human insulin is also denatured in aqueous solution. Additives which shift the aggregation equilibria of insulin in aqueous solution in the direction of the monomeric molecule, such as guanidine, urea, pyridine, or monomeric detergents, accelerate denaturation. Substances which shift the equilibria in the opposite direction, such as zinc and other divalent metal ions, retard denaturation. However, even a combination of all of the favorable conditions is not able to prevent the denaturation of insulin. This denaturation is observed even when solutions are stored at rest, although denaturation is slower in this case.

A special form of hydrophobic interfaces forms when aqueous solutions are frozen, for example in the lyophilization of proteins. At these interfaces the above described denaturation of proteins is also observed [U.B. Hansson, Acta Chem. Scand. 22, page 483 (1968)].

The denaturation can confer immunogenic properties upon a protein (i.e. the capability to induce immunological defense reactions in an organism) or intensify immunogenic properties already present. In addition, biological properties, such as enzymatic, serological or hormonic activities, can be modified or destroyed.

It is also known that the adsorption of proteins at interfaces forming between an aqueous solution and a liquid hydrophobic phase can be prevented by adding monomeric, surface-active substances, such as alkyl alcohols, to the system [cf. R. Cecil and C. F. Louis, Biochem. J. 117, page 147 (1970)]. These substances are themselves reversibly adsorbed at the hydrophobic interfaces and thus displace the proteins. The drawback of this process resides in the fact that the concentration of the surface-active substances must be near their limit of saturation in aqueous solution to ensure an optimum charge of the interface. In many cases the size of the interface is not constant but varies (for example the interface solution/air when stirring or shaking protein solutions) so that the aqueous solution alternately has to supply and take up molecules of said surface-active substances, that is to say it must contain a buffer stock. If the concentration necessary to be used is near the saturation limit, this is possible to a limited extent only.

Another drawback of this process is that the aforesaid monomeric, surface-active substances are adsorbed not only at the hydrophobic interfaces, but also at the hydrophobic zones of the dissolved proteins, where they bring about denaturation of the dissolved proteins which is irreversible in most cases and which should be avoided.

The strength of the bond of the monomeric, surface-active substances to the hydrophobic interfaces and to the hydrophobic zones of the dissolved proteins depends on the hydrophobicity of the substances, i.e., for example, on the length of the alkyl chains. The longer the alkyl chain, the faster the bond. The contradiction between as substantial as possible a charge of the interfaces with the surface-active substances (obtainable by a high hydrophobicity of the substances or a high concentration used) and as weak as possible a bond to the hydrophobic zones of the dissolved proteins appeared to be insolvable.

It has now been found that polymeric substances with alternatingly arranged hydrophobic and hydrophilic zones change the interfaces in such a manner that the adsorption of proteins at said interfaces and, consequently, the aforesaid secondary reactions such as interface aggregation, can be effectively avoided.

The method for stabilizing aqueous protein solutions as described in the present invention is generally applicable to peptides and polypeptides that are capable of being adsorbed out of a solution onto a hydrophobic interface. Among the peptides and polypeptides which may be used there may be mentioned enzymes such as uricase, lysozyme, streptokinase, myoglobin, neuraminidase, peptide hormonese such as secretin, glucagon, calcitonin, gastrin, ACTH, bradykinin, cholecystokinin, growth hormone, erytropoietin, thyroid stimulating hormones, thymosin, hypothalamic releasing factors, relaxine, as well as proteins with other functions e.g. albumin, immunoglobulins of different classes and species, fibroblast interferon, leukocyte interferon, and immune-induced interferon of human origin.

It is, therefore, the object of the presence invention to provide an aqueous protein solution characterized by a content of a surface-active substance with basic chain structure, the membes of which contain weakly hydrophobic and weakly hydrophilic zones in alternating arrangement. More particularly, the invention provides aqueous insulin solutions optionally containing the usual additives for the adjustment of isotonicity, preservation and/or causing a depot effect, which solutions additionally contain a surface-active substance as defined above.

Preferred surface-active substances in the sense of the present invention are homo-, co- or block polymers of the formula I

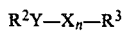

in which $X_n$ denotes a chain of n members of the formulae II and III

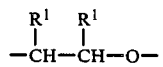

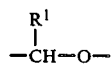

in any desired sequence and n is 2 to 80, preferably 8 to 45,

Y is —O— or —NH—

$R^1$ is H, —CH$_3$ or —C$_2$H$_5$, the radicals $R^1$ being identical or different, but in at least one half of the chain members X contains —CH$_3$ or —C$_2$H$_5$, and $R^2$ and $R^3$, independently of each other, are hydrogen or an organic radical.

Especially preferred are compounds of the formula I in which $R_2$ and $R_3$ denote hydrogen. Less preferred are compounds of formula I in which $R_3$ denotes alkyl with 1 to 20 carbon atoms, carboxyalkyl with 2 to 20 carbon atoms or alkylphenyl with 1 to 10 alkyl carbon atoms and $R^2$ denotes alkyl with 1 to 20 carbon atoms and, in the case of Y being —O—, also carboxalkyl with 2 to 20 carbon atoms or alkylphenyl with 1 to 10 alkyl carbon atoms.

Suitable radicals $R^2$ and $R^3$ are methyl, ethyl, propyl, or butyl, or the radicals derived from lauryl alcohol or myristyl alcohol: carboxyl alkyl groups derived from acetic acid, propionic acid, butyric acid, palmitic acid, or stearic acid: nonylphenoxy, oleylamino or stearylamino.

$R^2$ and $R^3$ can also derive from a polyhydric alcohol, such as glycerol or pentaerythritol or from a polybasic carboxylic acid, such as citric acid, or from a polyvalent amine, such as ethylene diamine. Members $R^2$ or $R^3$ of higher functionality may be linked with two or more polyalkoxy chains of the type defined above, whereby branched products are obtained.

The surface-active substances to be used according to the invention are produced in known manner by controlled addition of alkylene oxides on alkylene diglycols (or polyhydric alcohols or amines, such as pentaerythritol or ethylene diamine if branched products are desired). The terminal hydroxyl function may be subsequently esterified or etherified. A general description for the manufacture of a suitable block polymer is given in Example 1a.

The surface-active substances to be used according to the invention are characterized in that they are effective even in concentrations of 2 to 500 ppm, preferably 2 to 200 ppm, in aqueous media. It can be supposed that the interface of said substances has a form such that the hydrophobic groups protude into the hydrobobic phase and the hydrophilic groups in alternate arangement into the aqueous phase. Since the hydrophobicity of the individual hydrophobic groups is relatively weak, it can be assumed that the bonds of these individual hydrophobic groups to foreign hydrophobic structures, for example the hydrophobic zones of dissolved proteins, are so weak that they can be neglected at the low concentrations used according to the invention. It is only the sum of all the bonds of the individual hydrophobic groups to a larger hydrophobic surface (interface with respect to which the hydrophobic zones of the dissolved proteins are very small) that ensures an optimum covering of the interfaces even at low concentration.

It is assumed that the molecular form of the surface-active substances to be used according to the invention in aqueous solution differs from the form they acquire on the surface. In aqueous solution the polymer chain is formed in a manner such that the individual hydrophobic zones saturate one another and that the hydrophilic zones protrude to the outside into the aqueous surroundings. This results in a sufficiently high solubility in aqueous media so that a sufficient amount of stock buffer is present, which ensures, even with continuous change of the size of the interfaces, an optimum charge of the interfaces with the said substances.

The prevention of adsorption and denaturation by the additives according to the invention is the more surprising since, as described above, it is precisely the addition of monomeric, surface-active substances (detergents) which accelerates the denaturation of protein solutions, especially insulin solutions.

The polymeric, surface-active substances mentioned above can be added to a protein solution or the surfaces which are intended to come into contact with protein solutions are pretreated with these surface-active substances.

The addition of these polymeric, surface-active substances to protein solutions is not restricted to solutions for therapeutic purposes. These substances can also be added to protein solutions during processes for the preparation and purification of proteins in order to prevent adsorption and denaturation at interfaces, especially during gel chromatography and ultrafiltration.

The denaturation of insulin is a reversible process. It is possible to renature the denatured products by treating the denatured insulin with readily soluble detergents (for example sodium dodecyl sulfate), with aqueous alkaline media at a pH above 10.5 or with concentrated trifluoroacetic acid. It is thus possible, under the said conditions, to renature the small proportion of denatured insulin in the insulins obtained by the customary process of preparation, before the solutions of these products are brought into contact with the surface-active substances according to the invention.

Insulin solutions for therapeutic purposes can be prepared in accordance with the following general instructions of preparation:

Up to 1,500,000 I.U. of bovine, swine or human insulin, or of a De-B1-phenylalanine derivative of these insulins, which contain up to 0.8% by weight of zinc, are dissolved in 400 ml of water with the addition of 1N hydrochloric acid. The solution is mixed with 500 ml of a solution which contains a preservative, for example phenol, cresol or methyl p-hydroxybenzoate, an agent for rendering the solution isotonic, for example sodium chloride, glycerol, glucose, or a similar carbohydrate, and a salt for buffering the pH value, for example sodium phosphate, acetate, citrate, sodium veronal, or tris(hydroxymethyl)-aminomethane. In addition, the solution can also contain a depot assistant, such as Surfen, in order to obtain a delayed insulin action. The pH value is adjusted to 3.0–4.0 with 1N hydrochloric acid or to 6.8–7.5 with 1N sodium hydroxide solution. 50 ml of an aqueous solution containing 2 to 200 mg of a surface-active substance according to the invention are then added and the solution is made up to 1,000 ml with water.

An insulin solution of this type for therapeutic purposes can be mixed with a suspension which contains amorphous or crystalline insulin with delayed action.

The following examples illustrate the invention.

EXAMPLE 1

(a) A 10 liter glass flask with stirrer, heating bath, reflux condenser and means for dosing alkylene oxides under nitrogen is charged with 152.1 g of propylene glycol and 125 g of 40% potassium hydroxide solution and the water is removed by distillation in vacuo. 4,141 g of propylene oxide and 476 g of ethylene oxide are then added slowly and successively at 120° C. while stirring. When the reaction is terminated, the potassium hydroxide is neutralized by adding lactic acid. The readily volatile constituents are separated by distillation under reduced pressure and the reaction product is dehydrated. It has an average molecular weight of 2,000 (Dalton) and a content of polyoxyethylene of 10% by weight in the molecule.

(b) Two samples of 10 ml each of a 0.1% solution of bovine serum albumin and human albumin, respectively, in 0.01M phosphate buffer, pH 7, and two analogous samples containing as a stabilizer 10 ppm (calculated on the weight of the solution) of a block polymer consisting of a linear polypropylene glycol chain with an average molecular weight of 1,750 (Dalton), on which on each side 5% of polyethylene glycol had been added by polymerization, were shaken at 37° C. The two former samples became strongly turbid after 7 and 30 days, respectively, resulting from denatured protein. The two samples containing the stabilizer were still limpid after several month.

EXAMPLE 2

Ten samples of 10 ml each of a 0.01% solution of the enzyme β-galactosidase from *E. coli* in 0.01M phosphate buffer, pH 7, with $3 \times 10^6$ μU/ml were admixed stepwise with 10 to 100 mg of silicone oil AK 350 and the suspensions were shaken for 48 hours at 5° C. Emulsions were formed which could be separated into two phases by ultracentrifugation (40,000 g, 30 minutes, 4° C.). The enzyme activity in the aqueous phase was determined. It was found that the silicone oil emulsion had adsorbed up to 70% of the enzyme. The test was repeated in the presence of 100 ppm, calculated on the weight of the solution, of the following compound

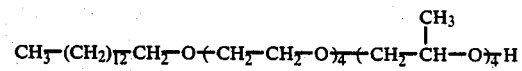

and it was found that no enzyme activity had been adsorbed on the silicone oil.

EXAMPLE 3

10 ml of an aqueous suspension of polystyrene beads (Dow-Latex®) having an average diameter of 0.481 μm were divided in two aliquots, one of which remained untreated while the other was shaken for 2 days at room temperature with 50 mg of a block polymer consisting of a linear polypropylene glycol chain with an average molecular weight of 2,250 (Dalton) on each side of which 5% of polyethylene glycol had been added by polymerization. The excess block polymer was then removed by dialysis against an aqueous solution containing 20 ppm of the same polymeric, surface-active substance.

Two times 3 ml portions of a solution of the proteins indicated in the following table in the given concentrations in phosphate buffer, pH 7, were prepared and each solution was shaken at 5° C. with 500 μl each of the untreated polystyrene suspension or the polystyrene suspension treated as described above, the latter still containing 20 ppm of the block polymer. Each sample was then filtered to clarity through a 0.2 μm filter. The table indicates the protein concentrations in the filtrates.

| Protein | protein A | concentration B | in solution C |
|---|---|---|---|
| Human-γ-globulin | 1.2 mg/ml | 1.20 mg/ml | 0.2 mg/ml |
| Egg-albumin | 0.5 mg/ml | 0.50 mg/ml | 0.22 mg/ml |

| Protein | protein A | concentration B | in solution C |
|---|---|---|---|
| Lysozyme | 1.0 mg/ml | 0.95 mg/ml | 0.25 mg/ml |
| Secretin | 1.0 mg/ml | 1.0 mg/ml | 0.3 mg/ml |
| Glucagon | 1.0 mg/ml | 0.9 mg/ml | 0.3 mg/ml |
| Insulin | 1.0 mg/ml | 1.0 mg/ml | 0.2 mg/ml |

A = 3 ml of the respective protein solution + 450 μl of buffer
B = after contact with treated polystyrene surfaces
C = after contact with untreated polystyrene surfaces.

The test was repeated at 37° C. The filtrates were additionally examined by gel chromatography in a column. It was found that the protein solutions which had been in contact with the untreated polystyrene beads contained high molecular weight aggregates, whereas such aggregates were not observed in the protein solutions contacted with the pretreated polystyrene beads.

EXAMPLE 4

5 Samples of 10 ml each of a 0.1% solution of glucagon in 0.05M Tris/HCl buffer, pH 8, and 5 analogous samples containing 50 ppm each, calculated on the weight of the solution, of the following compound

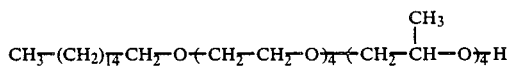

were shaken at room temperature. The former 5 samples had become turbid after 4 days as a result of precipitated denatured protein. The samples containing the surface-active substance remained clear for several weeks.

EXAMPLE 5

1-5 ml each of 0.1% solutions of the following peptide hormones: secretin, calcitonin, glucagon, gastrin, adrenocorticotropic hormone (ACTH), bradykinin, cholecystokinin (CCK), gastrin inhibiting polypeptide (GIP), vasoactive intestinal polypeptide (VIP) and luteinizing releasing hormone (LHR) in 0.05M Tris/HCl buffer, pH 7.5, and analogous samples containing 10 ppm, calculated on the weight of the solution, of a block polymer consisting of a linear polypropylene glycol chain with an average molecular weight of 2,000 (Dalton) on each side of which 5% of polyethylene glycol had been added by polymerization, were shaken at 37° C. After a few days, the samples without stabilizer had become turbid due to denatured protein, whereas the stabilized samples remained clear even after several months.

EXAMPLE 6

0.1% solutions of egg albumin, human immunoglobulin-G and myoglobin of the whale, respectively, in 0.01M phosphate buffer, pH 7, and analogous solutions containing 0.1%, calculated on the weight of the solution, of the following compound

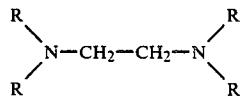

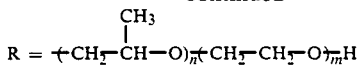

in which n and m are chosen to obtain a compound having an average total molecular weight of 12,500 Daltons with an ethylene oxide proportion of 40%, were freed from aggregates by ultracentifugation (for example 100,000 g/90 minutes). Ampules containing 10 ml each of the solutions were shaken at 37° C. The samples without stabilizer became strongly turbid after a few hours as a result of precipitated denatured protein. The samples containing the surface-active substance remained limpid for several months. When examined in an analytical ultracentrifuge, no new aggregate could be found.

EXAMPLE 7

Crystalline bovine insulin (40,000 I.U.) containing 0.5 percent by weight of zinc was dissolved in 200 ml of water with the addition of 3 ml of 1N hydrochloric acid. 700 ml of a solution of 1 g of methyl n-hydroxybenzoate, 16 g of glycerol and 1.4 g of sodium acetate.3H$_2$O were added to this solution. The pH of the solution was adjusted to 6.9–7.4 with 1N sodium hydroxide solution. After adding 5 ml of an aqueous 0.1% strength solution of linear polypropylene glycol with an average molecular weight of 2,000 (Dalton), the mixture was made up to 1,000 ml with water and the solution was sterile-filtered.

EXAMPLE 8

Crystalline De-B1-phenylalanine-insulin from cattle (100,000 I.U.) containing 0.6 percent by weight of zinc was dissolved in 200 ml of water with the addition of 3 ml of 1N hydrochloric acid. 700 ml of a solution of 2 g of phenol, 17 g of glycerol and 6.057 g of tris-(hydroxymethyl)-aminomethane the pH of which had been adjusted to 7.6 with 35 ml of 1N hydrochloric acid, were added to this solution. The pH of the solution was adjusted to 7.2–7.6. After adding 10 ml of an aqueous 1% strength solution of the compound

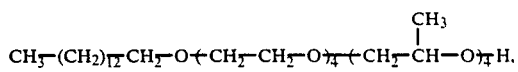

the mixture was made up to 1,000 ml with water and the solution was sterile-filtered.

EXAMPLE 9

Amorphous bovine insulin (1,000,000 I.U.) containing 0.8 percent by weight of zinc was dissolved in 400 ml of water with the addition of 5 ml of 1N hydrochloric acid. 500 ml of a solution of 2.5 g of phenol, 16 g of glycerol and 1.78 g of Na$_2$HPO$_4$.2H$_2$O were added to this solution. The pH of the solution was adjusted to 7.2–7.5. After adding 5 ml of an aqueous 0.1% strength solution of linear polypropylene glycol with an average molecular weight of 1.750 (Dalton), the mixture was made up to 1,000 ml with water and the solution was sterile-filtered.

EXAMPLE 10

Bovine insulin (40,000 I.U.), which had been purified by chromatography in the presence of a block polymer consisting of a linear chain of polypropylene glycol with an average molecular weight of 1,750 (Dalton) on each side of which 5% of polyethylene glycol had been copolymerized, and which contained 0.6 percent by weight of zinc, was dissolved in 200 ml of water with the addition of 3 ml of 1N-hydrochloric acid. 700 ml of a solution of 2.5 g of m-cresol, 50 g of glucose, 1.4 g of sodium acetate.3H$_2$O and 10 mg of the abovementioned block polymer were added to this solution. The pH of the solution was adjusted to 6.9–7.4 with 1N sodium hydroxide solution and the solution was made up to 1,000 ml with water and sterile-filtered.

EXAMPLE 11

Crystalline swine insulin (40,000 I.U.) containing 0.6 percent by weight of zinc was dissolved in 200 ml of water with the addition of 3 ml of 1N HCl. 700 ml of a solution of 1 g of methyl p-hydroxybenzoate, 17 g of glycerol, 1.4 g of sodium acetate.3H$_2$O and 10 mg of a linear polypropylene glycol with an average molecular weight of 1,750 (Dalton) were added to the solution. The pH of the solution was adjusted to 6.9–7.4. The solution was made up to 1,000 ml with water and sterile-filtered.

EXAMPLE 12

Crystalline bovine insulin (450,000 I.U.), which had been purified by one of the customary chromatography processes in the presence of a block polymer consisting of a linear chain of polypropylene glycol with an average molecular weight of 1,750 (Dalton) on each side of which 5% of polyethylene glycol had been copolymerized, and which contained 0.5 percent by weight of zinc, was dissolved in 400 ml of 0.03N hydrochloric acid. A solution of 150 mg of ZnCl$_2$ and 5 mg of the block copolymer used for chromatography, in 100 ml of 0.03N HCl was added to this solution. The solution was sterile-filtered and mixed with 500 ml of a solution, which was likewise sterile-filtered, of 70 g of NaCl, 14 g of sodium acetate.3H$_2$O, 5 mg of the block polymer used for chromatography and 10 ml of 1N NaOH in water. The pH of the mixture was adjusted to 5.4 and the mixture was stirred for 48 hours at room temperature, during which period the insulin crystallized in rhombohedra. 10.25 l of a sterile solution of 20 g of NaCl, 1.75 g of sodium acetate.3H$_2$O, 11.25 g of methyl p-hydroxybenzoate and 102.5 mg of the block polymer used for chromatography were added to the crystal suspension. The pH was adjusted to 6.9–7.3 by the dropwise addition of 1N NaOH.

EXAMPLE 13

Crystalline bovine insulin (40,000 I.U.), which had been purified by one of the customary chromatography processes in the presence of the compound

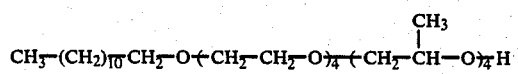

and which contained 0.5 percent by weight of zinc, was dissolved in 200 ml of water with the addition of 3 ml of 1N hydrochloric acid. 700 ml of a solution of 1 g of methyl p-hydroxybenzoate, 50 g of glucose, 0.175 g of Surfen and 100 mg of the substance used for chromatography were added to this solution. The pH of the solution was adjusted to 3.3–3.5 if necessary, using 1N HCl or 1N NaOH, and the solution was made up to 1,000 ml with water and sterile-filtered.

EXAMPLE 14

Five samples of 1.5 ml each of a solution of 5000 units of human fibroblast interferon in phosphate buffer, pH 7, and five analogous samples containing as a stabilizer 10 ppm (calculated on the weight of the solution) of a block polymer consisting of a linear chain of 1.2-polypropylene glycol with an average molecular weight of 1750 (Dalton), to which on each side 5% polyethylene glycol had been attached by polymerisation, were shaken at 37° C. In the five former samples a loss of more than 97% of the biological activity was determined after 2 days. The biological activity of the interferon in the five samples containing the stabilizer was found to be unchanged, even after several weeks.

The test was repeated at room temperature, showing a similar loss of the biological activity in the unstabilized samples after 5 days. In the samples containing the stabilizer the activity of the interferon again remained unchanged after several weeks.

EXAMPLE 15

10 ml of an aqueous suspension of polystyrene beads (Dow Latex ®) having an average diameter of 0.481 μm were divided in two aliquots, one of which remained untreated, while the other was shaken for two days at room temperature with 50 mg of block polymer consisting of a linear 1.2-polypropylene glycol chain with an average molecular weight of 1750 (Dalton), to which on each side 10% of polyethylene glycol had been attached by polymerisation. The excess block polymer was then removed by dialysis against an aqueous solution containing 150 ppm of the same polymeric, surface-active substance.

Two samples of 3 ml each of a solution of 10 000 units of human fibroblast interferon in a phosphate buffer, pH 7, were prepared and each soluton was shaken at 5° C. for 20 hours with 500 μl each of the untreated polystyrene suspension or the polystyrene suspension treated as described above, the latter still containing 150 ppm of the block polymer. Each sample was then filtered to clarity through a 0.2 μm filter. The biological activity of the interferon in the filtrate was determined. In the solutions which were in contact with the untreated polystyrene beads, less than 1% of the calculated activity was determined. In the solutions which were in contact with the polystyrene beads treated as described above, more than 95% of the activity which was determined at the beginning of the test were retained.

EXAMPLE 16

Two vials each filled with 10 ml of a solution of human insulin (500 units per ml) in 0.05M Tris/HCl-buffer, pH 7, and two analogous samples containing as a stabilizer 10 ppm (calculated on the weight of the solution) of a block polymer consisting of a linear 1.2-polypropylene glycol chain with an average molecular weight of 1750 (Dalton), to which on each side 5% of polyethylene glycol had been attached by polymerisation, were shaken at 37° C. The two former samples became strongly turbid after 5 days, resulting from denatured insulin, and the biological activity of the hormone had dropped to less than 10% of the activity which was determined at the beginning of the test. The two samples containing the stabilizer remained clear even after more than 1 year and the biological activity was determined to be unchanged.

What is claimed is:

1. A method for stabilizing an aqueous solution of a water soluble biologically active protein to motion conditions, said solution having a pH between 6.8 and 8, which method comprises adding to said solution from 2 to 500 ppm of a surface active compound of the formula $$R^2Y-X_n-R^3$$

wherein
$X_n$ is a chain of n members selected from the group of members having the formulas $$-\underset{\underset{R^1}{|}}{CH}-\underset{\underset{R^1}{|}}{CH}-O- \quad \text{and} \quad -\underset{\underset{R^1}{|}}{CH}-O-,$$

in any sequence,
n is 2 to 80,
Y is —O— or —NH—,
$R^1$ is —H, —$CH_3$, or —$C_2H_5$, and may be the same or different but is such that at least one-half of the members of the chain $X_n$ contains —$CH_3$ or —$C_2H_5$, and
$R^2$ and $R^3$ are each members independently selected from the group consisting of hydrogen, alkyl having 1 to 20 carbon atoms, carboxyalkyl having 2 to 20 carbon atoms, and alkylphenyl having 1 to 10 carbon atoms, but wherein $R^2$ may only be such alkyl if Y is —NH—.

2. A method as in claim 1 wherein said biologically active protein is bovine insulin, swine insulin, human insulin, or a De-$B_1$-phenylalanine derivative of such an insulin which contains up to 0.8 percent of zinc by weight of said insulin or derivative.

3. A method for stabilizing an aqueous solution of a water soluble biologically active protein to motion conditions, said solution having a pH between 6.8 and 8, which method comprises adding to said solution from 2 to 200 ppm of a surface active compound of the formula $$R^2Y-X_n-R^3$$

wherein
$X_n$ is a chain of n members selected from the group of members having the formulas $$-\underset{\underset{R^1}{|}}{CH}-\underset{\underset{R^1}{|}}{CH}-O- \quad \text{and} \quad -\underset{\underset{R^1}{|}}{CH}-O-.$$

in any sequence,
n is 2 to 80,
Y is —O— or —NH—,
$R^1$ is —H, —$CH_3$, or —$C_2H_5$, and may be the same or different but is such that at least one-half of the members of the chain $X_n$ contains —$CH_3$ or —$C_2H_5$, and
$R^2$ and $R^3$ are each members independently selected from the group consisting of hydrogen, alkyl having 1 to 20 carbon atoms, carboxyalkyl having 2 to 20 carbon atoms, and alkylphenyl having 1 to 10 carbon atoms, but wherein $R^2$ may only be such alkyl if Y is —NH—.

4. A method as in claim 3 wherein said biologically active protein is bovine insulin, swine insulin, human insulin, or a De-$B_1$-phenylalanine derivative of such an insulin which contains up to 0.8 percent of zinc by weight of said insulin or derivative.

5. A method as in claim 3 wherein $R^2$ and $R^3$ are each hydrogen and Y is oxygen.

6. A method as in claim 3 wherein said biologically active protein is insulin.

7. A method as in claim 4 wherein said solution additionally contains at least one member selected from the groups consisting of agents rendering said solution isotonic, preservatives, and buffers.

8. A method as in claim 4 wherein said solution additionally contains a depot component providing a delayed action release for said insulin or derivative.

* * * * *